United States Patent
Fujita et al.

(10) Patent No.: US 9,457,170 B2
(45) Date of Patent: Oct. 4, 2016

(54) BALLOON AND BALLOON CATHETER

(71) Applicant: TERUMO KABUSHIKI KAISHA, Tokyo (JP)

(72) Inventors: Yotaro Fujita, Fujinomiya (JP); Makoto Onishi, Fujinomiya (JP); Naoyuki Maeda, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 806 days.

(21) Appl. No.: 13/731,254

(22) Filed: Dec. 31, 2012

(65) Prior Publication Data
US 2013/0190690 A1    Jul. 25, 2013

(30) Foreign Application Priority Data

Jan. 23, 2012   (JP) .................. 2012-011534

(51) Int. Cl.
*A61M 25/10*   (2013.01)
*B29C 47/06*   (2006.01)
*A61M 25/00*   (2006.01)
(Continued)

(52) U.S. Cl.
CPC .............. *A61M 25/10* (2013.01); *A61L 29/06* (2013.01); *A61L 29/085* (2013.01); *A61L 29/14* (2013.01); *A61M 25/005* (2013.01); *A61M 25/104* (2013.01); *A61M 25/1029* (2013.01); *B29C 47/065* (2013.01); *A61L 2420/08* (2013.01); *A61M 2025/1075* (2013.01); *Y10T 428/1352* (2015.01)

(58) Field of Classification Search
CPC ........... A61M 25/10; A61M 25/1029; A61M 25/104; Y10T 428/1334; Y10T 428/1352; B29C 47/0023; B29C 47/0054; B29C 47/06; B29C 47/065; B29C 49/04; B29C 49/08; B29C 49/22
See application file for complete search history.

(56) References Cited

U.S. PATENT DOCUMENTS 5,648,450 A * 7/1997 Dickens, Jr. .......... B29C 41/003
                                                        156/62.2
5,769,817 A   6/1998 Burgmeier
(Continued)

FOREIGN PATENT DOCUMENTS

| EP | 0 768 097 A2 | 4/1997 |
|----|--------------|--------|
| EP | 2 055 342 A1 | 5/2009 |
| JP | 4-93323 A    | 3/1992 |
| JP | 9-164191 H   | 6/1997 |
| JP | 2005-230578 A | 9/2005 |

(Continued)

OTHER PUBLICATIONS

The extended European Search Report dated Apr. 13, 2013, issued in corresponding European Patent Application No. 13152143.7. (4 pages).

(Continued)

*Primary Examiner* — Walter B Aughenbaugh
(74) *Attorney, Agent, or Firm* — Buchanan Ingersoll & Rooney PC (57) ABSTRACT

A balloon including a laminated film of at least two layers including a polyamide elastomer layer and a polyamide layer wherein the polyamide elastomer layer is formed at the inner side of the polyamide layer and a molecular weight distribution of the polymers as a whole of the balloon (weight-average molecular weight $M_w$/number-average molecular weight $M_n$) ranges from 3 to 10.

18 Claims, 3 Drawing Sheets

(51) Int. Cl.
*A61L 29/06* (2006.01)
*A61L 29/08* (2006.01)
*A61L 29/14* (2006.01)

(56) References Cited

U.S. PATENT DOCUMENTS

| | | | |
|---|---|---|---|
| 6,488,688 B2 | 12/2002 | Lim et al. | |
| 2003/0135018 A1* | 7/2003 | Way | C08G 69/34 528/310 |
| 2008/0090975 A1 | 4/2008 | Yokoyama et al. | |
| 2010/0228000 A1* | 9/2010 | Waibel | C08J 11/08 528/310 |
| 2010/0262218 A1 | 10/2010 | Deshmukh | |
| 2011/0301290 A1 | 12/2011 | Kato et al. | |

FOREIGN PATENT DOCUMENTS

| | | |
|---|---|---|
| JP | 2005-246097 A | 9/2005 |
| JP | 2005/319289 A | 11/2005 |
| JP | 2012-010846 A | 1/2012 |
| WO | 02/36196 A1 | 5/2002 |
| WO | 2006/059536 A | 6/2006 |
| WO | 2010/098335 A | 9/2010 |

OTHER PUBLICATIONS

Japanese Official Action issued Sep. 15, 2015, by the Japan Patent Office, in corresponding Japanese Patent Application No. 2012-011534 with English translation (7 pages).

* cited by examiner

BALLOON AND BALLOON CATHETER

CROSS REFERENCE TO RELATED APPLICATION

This application claims priority under 35 U.S.C. §119 to Japanese Patent Application No. 2012-11534 filed Jan. 23, 2012, the entire content of which is incorporated hereby by reference.

TECHNICAL FIELD

The disclosure here generally pertains to a balloon and a balloon catheter. The disclosure here more specifically pertains to a balloon and a balloon catheter both configured to be inserted into the lumen in a living body.

BACKGROUND DISCUSSION

Where a stent is indwelled at a stenosed lesion area of a living body lumen such as a blood vessel, biliary duct, esophagus, trachea, urethra and other organs to secure the lumen, catheters attached with a balloon (i.e., balloon catheters) can be used for treating ischemic heart disease or for urethral catheterization for a patient who has difficulty urinating.

It can be desirable for the balloon for catheter to have various characteristics including (1) trackability (ability to track meandering blood vessels), (2) ability to pass through a stenosed lesion such as in blood vessels), (3) ability to dilate a stenosed lesion such as in calcified blood vessels, (4) a compliance characteristic (an appropriate degree of non-distensibility sufficient for not causing a great change in balloon diameter depending on a small pressure change) and strength or pressure resistance sufficient to withstand an inner pressure or impact upon balloon inflation.

It can be desirable for catheter balloons to have such safety that the possibility of causing damages against a blood tumor or blood vessel can be minimized as small as possible. Accordingly, a characteristic of not causing a great change in balloon diameter depending on a small change in pressure, i.e., a compliance characteristic, can be one of the most important characteristics. A technique in which attention has been paid to this compliance characteristic is described, for example in U.S. Pat. No. 6,488,688 B2. In U.S. Pat. No. 6,488,688 B2, there is proposed a semi-flexible balloon formed of a polyurethane block copolymer and showing a rate of change of 0.025 to 0.045 mm/atm within an inflation pressure range of from 6 atm to 19 atm, and an axially inflexible balloon formed of a polyurethane block copolymer and showing a rate of change of 0.01 to 0.25 mm/atm within an inflation pressure range of 6 atm to 14 atm.

Other technology is proposed in U.S. Pat. No. 5,769,817. In U.S. Pat. No. 5,769,817, a balloon, which is formed of a double-wall tubular member constituted of a polyamide for the outermost wall and polyethylene terephthalate for the innermost wall, shows a compliance coefficient of not larger than 13% over a pressure range of 8 to 18 atm.

It is stated in U.S. Pat. No. 5,769,817 that this balloon is able to suppress the wear ascribed to the frictional phenomenon between the balloon and a stent when in use for stent delivery and is excellent in non-distensibility contributing to suppress excess expansion of a stent against blood vessel and also in burst strength.

SUMMARY

As stated above, the balloon of U.S. Pat. No. 6,488,688 B2 has been made from the standpoint of suppressing and preventing the folded balloon from causing non-uniform expansion of a stent. To this end, the balloon is formed by use of a single-layer film made of a semi-flexible polyurethane copolymer in place of an inflexible material showing non-distensibility, such as a nylon (polyamide). However, since the outer wall brought in contact with a living body is made of a polyurethane copolymer, trackability and the ability to pass through a stenosed lesion are impaired although the non-uniform expansion can be suppressed. Additionally, since a semi-flexible material is used, non-distensibility is not guaranteed in the course of the inflation of the balloon in a living body, thus leaving a safety concern.

In U.S. Pat. No. 5,769,817, the balloon is formed of a laminated film including a polyethylene terephthalate layer of high strength material at an inner wall side and polyamide layer, which is more flexible than the polyethylene terephthalate, at the outer wall side. In order to raise trackability, the balloon is formed as a thin film. Accordingly, there is a concern that the balloon suffers from breakage in a living body when brought in contact with a stone or calcified stenosed lesion.

The disclosure here provides a balloon and a balloon catheter exhibiting improved compliance characteristics without significantly sacrificing pressure resistance performance and passage performance.

According to one aspect, when polymers constituting a balloon film as a whole are macroscopically taken into account irrespective of the molecular weight and its distribution of a polymer in every layer forming the balloon, the compliance characteristic can be improved without a sacrifice of pressure resistance and passage performance, provided that the molecular weight distribution of the polymers as a whole of the balloon is within a predetermined range.

According to an exemplary aspect, a compliance of the balloon, which indicates the ease in radial inflation, is as low as not larger than 0.013 mm/atm (i.e., a compliance characteristic is improved), so that the elongation at a balloon portion under pressurized conditions can be drastically suppressed while keeping the pressure resistance and passage performances.

According to an exemplary aspect, disclosed is a balloon comprising a laminated film of at least two layers including a polyamide elastomer layer and a polyamide layer, wherein said polyamide elastomer layer is formed at an inner side of said polyamide layer, wherein a molecular weight distribution of the polymers as a whole of said balloon, calculated by weight-average molecular weight Mw/number-average molecular weight Mn, is in a range of 3 to 10.

According to an exemplary aspect, disclosed is a balloon catheter comprising an exemplary balloon described herein.

Another aspect of the disclosure here involves a method of making a balloon, the method comprising: forming a multi-layered polymer tube by co-extrusion of a polyamide layer and a polyamide elastomer layer, axially stretching the tube at a temperature in a range of from 25° C. to less than each melting point of the polyamide of the polyamide layer and the polyamide elastomer of the polyamide elastomer layer, biaxially stretching the stretched tube by radial inflation, and cooling the tube.

DETAILED DESCRIPTION

According to an embodiment disclosed by way of example (exemplary embodiment), there is provided a balloon formed of a laminated film of at least two layers including a polyamide elastomer layer and a polyamide layer wherein the polyamide elastomer layer is formed at the inner side of the polyamide layer and a molecular weight distribution of the polymers as a whole of the balloon (weight-average molecular weight Mw/number-average molecular weight Mn) ranges from 3 to 10.

This can enable the balloon to be improved in compliance characteristic (i.e. a compliance becomes not larger than 0.013 mm/atm) while maintaining pressure resistance and passage performance. Elongation at a balloon portion under pressurized conditions can be drastically suppressed, so that not only a lesion can be reliably dilated, but also damage on mucosa or the inner surface of blood vessel can be suppressed. When a lesion where a stent is indwelled is dilated, the breakage of the stent per se can be mitigated or prevented.

The term "compliance" indicates the ease in radial inflation, and indicates an inclination of a compliance curve showing a relation with a radial (a diameter of the balloon) increase at the time when an internal pressure within a working range of 12 atm to 22 atm is applied.

Figure 1A:
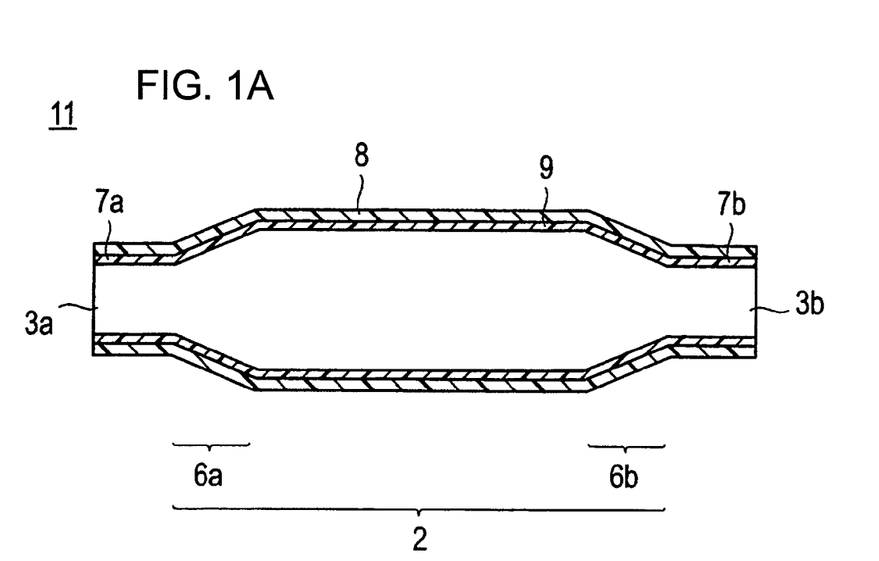
FIG. 1A is a schematic view showing a balloon, according to an exemplary embodiment.
Figure 1B:
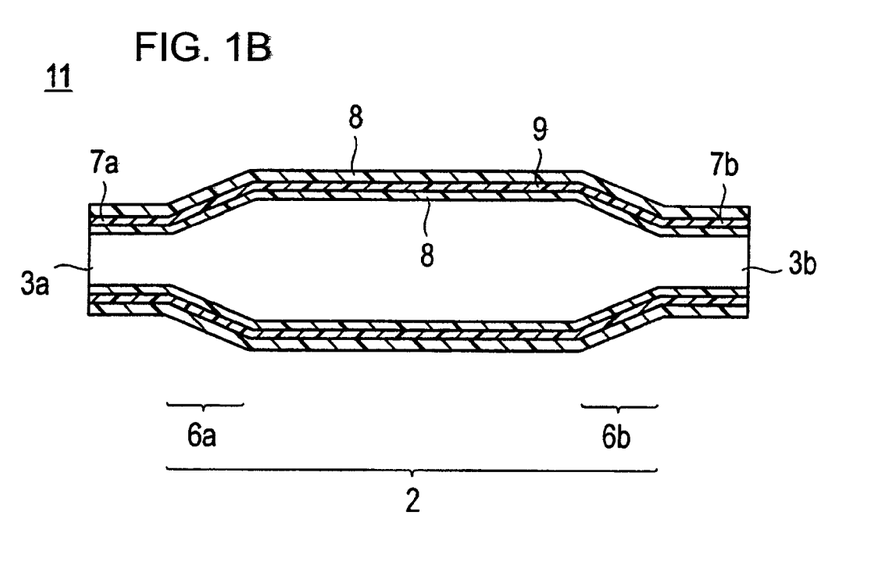
FIG. 1B is a schematic view showing a balloon, according to another exemplary embodiment.

The structure of an exemplary balloon is now described with reference to the accompanying drawings. FIGS. 1A and 1B are, respectively, examples of the balloon although the balloon should not be construed as limited thereto.

[Balloon]

FIG. 1A is a sectional view showing a balloon according to an exemplary embodiment, which has a double layer structure including a polyamide layer and a polyamide elastomer layer. FIG. 1B is a sectional view showing a balloon according to another exemplary embodiment, which has a three-layer structure having a polyamide elastomer layer, a polyamide layer and a polyamide elastomer layer laminated successively.

In the figures, a balloon 11 can be configured to include a tubular film body 2 capable of being inflated or deflated by means of a fluid supplied from a catheter, and connection portions 7a, 7b axially extending from opposite sides of the film body and connected with the catheter. The connection portions 7a, 7b at the opposite ends are, respectively, formed with openings 3a, 3b to be inserted from the catheter. The opening 3b of one connection portion can be formed larger in diameter than the opening 3a of the other connection portion. The balloon 11 has a tubular portion having substantially a uniform outer diameter so as to dilate a stenosed portion of a lumen in a living body, such as a blood vessel, ureter, bile duct or the like.

Further, the opposite end portions of the tubular film body may be tapered as shown in FIGS. 1A and 1B. The balloon can have a tubular film body provided with tapered portions 6a, 6b tapered toward opposite ends, and connection portions 7a, 7b adjoining to the tapered portions 6a, 6b, respectively, and axially outwardly extending for connection with a catheter. In addition, the connection portions 7a, 7b at the opposite ends are, respectively, formed with openings 3a, 3b to be inserted from the catheter.

Where the opposite end portions of the tubular film body are tapered, the central portion of the tubular film body is configured to have a maximum diameter of the balloon that is greater than the tapered portions 6a, 6b. For example, the tapered portions 6a, 6b are contiguous to the central portion of the tubular film body and the diameter thereof is so changed as to be continuously reduced toward the respective ends.

Further, the connection portions 7a, 7b with the catheter are, respectively, contiguously connected to the tapered portions 6a, 6b and are smaller-diameter portions whose outer diameter is substantially uniform. The connection portions 7a, 7b serve each as an attachment of the balloon to the catheter and are, respectively, formed with the openings 3a, 3b. The tapered portions 6a, 6b and the connection portions 7a, 7b to be connected with the catheter are, respectively, provided at opposite sides of the tubular film body of the balloon. The tapered portions and the connection portions may differ in shape from each other, respectively.

An exemplary balloon is formed of a film having a multi-layered structure wherein at least two layers made up of a polyamide elastomer layer and a polyamide layer are laminated. For example, the balloon can be formed of a film having one to three polyamide elastomer layers and one to three polyamide layers. For example, the balloon can be formed of a film having two polyamide elastomer layers and one polyamide layer.

When a polyamide elastomer and a polyamide are laminated in such a way as mentioned above, a parison described hereinafter can be readily produced by co-extrusion. Additionally, flexibility/passage performance and a pressure resistance performance for use as a balloon can be well balanced.

The order of lamination of the polyamide elastomer layer or layers and the polyamide layer or layers can be such that if a polyamide elastomer layer is formed as an innermost layer and a polyamide layer is formed on the surface of the polyamide elastomer layer (at an outer side of the polyamide layer), no limitation is placed on the other layer or layers with respect to the order of lamination. In an exemplary balloon, a polyamide elastomer layer can be formed at an outer side of the polyamide layer.

An exemplary balloon can be constituted of a film of a three-layered structure including a polyamide elastomer layer, a polyamide layer and a polyamide elastomer layer laminated successively in this order, wherein the outermost layer can be a polyamide elastomer layer.

For example, where the outermost layer is formed of a polyamide elastomer that is more flexible than a polyamide, the resulting balloon does not undergo breakage when brought into contact with a hard, sharp lesion such as a calcified lesion.

Furthermore, a biocompatible material or antithrombotic material may be covered, if desired, on the surface of a polyamide elastomer layer or polyamide layer provided as an outermost layer. As the biocompatible or antithrombotic material, a variety of known polymers may be used singly or in admixture. Specific examples of the polymer conveniently usable include natural polymers such as collagen, gelatin, chitin, chitosan, cellulose, polyaspartic acid, polyglutamic acid, polylysine, casein and the like, and synthetic polymers such as phospholipid polymer, MPC (methacryloyloxyethylphosphoryl choline) block polymer having a phosphate group at a side chain, polyhydroxyethyl methacrylate, copolymers of hydroxyethyl methacrylate and styrene (e.g. HEMA-St-HEMA block copolymer), polymethyl methacrylate, polylactic acid, polyglycolic acid, lactic acid-glycolic acid copolymer, polyethylene, polypropylene and the like.

In order to allow easy insertion of an exemplary balloon into a blood vessel or guide catheter, the outer surface of the balloon can be treated to develop lubricity when in contact with blood. Such a treatment can include a method of coating or fixing a hydrophilic resin on the surface. Such resins include, for example, poly(2-hydroxyethyl methacrylate), polyhydroxyethyl acrylate, hydroxypropyl cellulose, methyl vinyl ether/maleic anhydride copolymer, polyethylene glycol, polyacrylamide, polyvinylpyrrolidone, random or block copolymer of dimethylacrylamide/glycidyl methacrylate and the like.

For example, a polyamide elastomer layer can be formed in intimate contact with the surface of the polyamide layer. The polyamide elastomer layer can be formed in intimate contact with the whole surface of the polyamide layer.

This can allow for the provision of a balloon that does not suffer breakage when in contact with a hard, sharp lesion such as a calcified lesion and is improved in pressure resistance.

In an exemplary balloon, the molecular weight distribution of the polymers as a whole of the balloon (weight-average molecular weight/number-average molecular weight) is 3 to 10, for example, 3 to 8, for example, 3 to 7.

For example, if the molecular weight distribution is less than 3, the weight-average molecular weight as a whole of the balloon becomes small, thus leading to the lowering of both a burst pressure of balloon and a compliance characteristic. On the other hand, for example, if the molecular weight distribution exceeds 10, the molecular chain lengths in the respective layers of the balloon differ from one another and hence, there exist molecules having different chain lengths, with the result that structural defects originate from randomly existing molecular chain ends to allow fracture to proceed, with concern that the pressure resistance performance lowers.

The term "molecular weight distribution as a whole of the balloon (weight-average molecular weight/number-average molecular weight)" does not mean molecular weight distributions of individual polymers in the respective layers of the film, but means a molecular weight distribution of all polymers used in the film making up the balloon. In this regard, however, if a biocompatible material, antithrombotic material and/or a hydrophilic resin as described herein are coated on the balloon surface, the molecular weight distributions of these materials are not included in determining the "molecular weight distribution as a whole of the balloon (weight-average molecular weight/number-average molecular weight)". For example, with an exemplary balloon which is formed of a film of a multi-layered structure wherein at least two layers including a polyamide elastomer layer and a polyamide layer as stated before are laminated, a molecular weight distribution of all polymers constituting the multi-layered structure is meant. For instance, with the double-layered structure shown in FIG. 1A, a molecular weight distribution of all of the polymers constituting the two layers is meant, and with the three-layered structure shown in FIG. 1B, a molecular weight distribution of all of the polymers constituting the three layers is meant. The molecular weight distribution as a whole of the balloon can be controlled, for example, by controlling polymerization conditions. For instance, the molecular weight distribution can be appropriately controlled, for example, by changing polymerization temperatures.

The molecular weight distribution as a whole of balloon (weight-average molecular weight/number-average molecular weight) can be such that in a molecular weight distribution function plotting the molecular weight and the number of molecules, the resulting profile has a single peak. For the distribution profile, mention is made of a Poisson distribution, a Shultz-Flory distribution and the like. The molecular weight distribution can have "weight-average molecular weight/number-average molecular weight" working for the Shultz-Flory distribution.

The molecular weight distribution (weight-average molecular weight/number-average molecular weight) is indicated as a value obtained by measuring weight-average molecular weight (Mw) and number-average molecular weight (Mn) by a gel permeation chromatographic (GPC) method and dividing Mw by Mn. The measuring conditions of the GPC method include, for example, those conditions indicated below.

(1) Pretreatment: filtration through a 0.2 μm membrane filter
(2) Apparatus: pump Shodex DS-4
(3) Separation column: Shodex GPC HFIP-806M-+HFIP-803 (made by Showa Denko K.K.)
(4) Measuring temperature: 40° C.
(5) Carrier: hexafluoroisopropanol (+5 mmols/liter $CF_3COONa$)
(6) Flow rate: 1.0 ml/minute
(7) Injection amount: 100 μl
(8) Detector: Shodex RI-71 (made by Showa Denko K.K.)
(9) Concentration: 0.1 w/v%
(10) Standard substance for molecular weight: standard polymethyl methacrylate, dimethyl terephthalate The size of an exemplary balloon can be 1 to 35 mm, for example, 1.5 to 30 mm, with respect to an outer diameter of the tubular film body inflated. The length along the axial direction of the tubular film body can be 3 to 80 mm, for example, 10 to 75 mm, and the total length of the balloon (i.e., a total length along the axial direction of the tubular film body and the connection portions) can be 5 to 120 mm, for example, 15 to 100 mm.

The cross-sectional shape perpendicular to the axis of the balloon may be, for example, circular, ellipsoidal, substantially ellipsoidal or polygonal.

The average thickness of the balloon under deflated conditions can be 5 to 50 μm, for example, 10 to 30 μm.

An average thickness of the deflated balloon within a range of 5 to 50 μm can be desirable from the standpoint of trackability and the ability to pass through a stenosed lesion such as of the blood vessel or body cavity.

The connection portions of the balloon may be integrated with the film body 2 (or integrally molded), or may be formed by bonding, to the film body 2, a separate, substantially cylindrical film body whose diameter is smaller than the film body 2.

The balloon can be provided with the film body capable of being inflated and deflated by means of a fluid supplied from a catheter and can thus be foldable. In a deflated condition, the balloon is in a folded state around the outer periphery of the body tube of the catheter.

The balloon can be formed of a film, which is made of a laminate of at least two layers including a polyamide elastomer layer and a polyamide layer. The polyamide elastomer layer and polyamide layer serving as constituent elements of the balloon are now described.

(Polyamide Layer)

The average thickness of the polyamide layer of the balloon can be 0.5 to 49.5 µm, for example, 5 to 25 µm. For example, such range of the average thickness can enable the balloon to be balanced with respect to the flexibility/passage performance and the pressure resistance performance.

The polyamide layer contains a polyamide and may further contain known additives and a radio-opaque material, if desired, and may be constituted of a polyamide alone. For example, in the polyamide layer, if a polyamide is present in an amount of 50 to 100 wt %, a desirable pressure resistance and a compliance characteristic of the balloon can be attained.

The polyamide used in the polyamide layer can have an acid amide bond (—CO—NH—) in the main chain. In general, the polyamide can be prepared by polymerization (or homopolymerization) of a lactam or amino acid having a ring structure, or by condensation polymerization of a dicarboxylic acid and a diamine. A homopolymer can be used. As a monomer capable of being polymerized with itself, examples can include ε-caprolactam, aminocaproic acid, enantholactam, 7-aminoheptanoic acid, 11-aminoundecanoic acid, 12-aminododecanoic acid, 9-aminononoic acid, piperidine and the like.

The dicarboxylic acid used for condensation polymerization of a dicarboxylic acid and a diamine can include adipic acid, sebacic acid, dodecanedicarboxylic acid, glutaric acid, terephthalic acid, 2-methylterephthalic acid, isophthalic acid, naphthalenedicarboxylic acid and the like. The diamine can include tetramethylenediamine, hexamethylenediamine, nonamethylenediamine, decamethylenediamine, undecamethylenediamine, dodecamethylenediamine, paraphenylenediamine, metaphenylenediamine and the like.

The polyamide can include nylons 4, 6, 7, 8, 11, 12, 6.6, 6.9, 6.10, 6.11, 6.12, 6T, 6/6.6, 6/12, 6/6T, 6T/6I and the like.

The polyamides may be capped at terminal ends thereof with a carboxyl group, an amino group or the like. These polyamides may be used singly or in combination of two or more.

For example, the polyamide can be nylon 11 or nylon 12.

The weight-average molecular weight of the polyamide can be 10,000 to 500,000, for example, 15,000 to 400,000, for example, 20,000 to 300,000.

For example, when the weight-average molecular weight of a polyamide used as the polyamide layer is within a range of 10,000 to 500,000, ductility is good and a good compliance characteristic as a whole of the balloon is shown.

The weight average-molecular weight of the polyamide can be measured by known methods including an MS spectral method, a light scattering method, liquid chromatography such as GPC, gas chromatography and the like. The molecular weight used herein is one measured by the GPC method. The measuring conditions are the same as those used to calculate Mw/Mn as a whole of the balloon and are not indicated again.

Additives to be added to the polyamide layer, if desired, can include a higher alcohol, a hydroxybenzoic acid ester, an aromatic sulfonamide and the like, although not always limited to those indicated above.

A radio-opaque material to be contained in the polyamide layer, if desired, can be employed. The radio-opaque material is opaque to X-ray, and known radio-opaque materials can be used. For example, the radio-opaque material can include iodine, bismuth, barium, boron, bromine, calcium, gold, platinum, silver, iron, manganese, nickel, gadolinium, dysprosium, tungsten, tantalum, stainless steels, nitinol, barium sulfate or compounds thereof, and solutions/dispersions thereof (e.g., physiological saline solution); amidotrizoic acid (3,5-diacetamino-2,4,6-triiodobenzoic acid), meglumine sodium amidotrizoate, meglumine amidotrizoate, sodium iothalamate, meglumine iothalamate, meglumine iotroxate, iotrolan, ioxaglic acid, ioxilan, iopamidol, iopromide, iohexol, ioversol and iomeprol; and ethyl esters of iodized poppy acid fatty acids (e.g., Lipiodol (registered tradename), which is a poppy seed oil whose carbon atom is iodized). These radio-opaque materials may be used singly or in admixture of two or more. A radio-opaque layer using the above-indicated radio-opaque material as a base may be further laminated on the film body.

This can allow the degree of balloon inflation to be confirmed under radiography, so that the position of the balloon can be reliably, readily confirmed.

As to the section perpendicular to the axis of the balloon at the axial center thereof, a ratio of the sectional area of one polyamide layer to the total sectional area of the balloon can be 40 to 90%, for example, 50 to 75%.

For example, when the ratio is within this range, the molecular weight distribution as a whole of the balloon can be readily set in the range of 3 to 10.

(Polyamide Elastomer Layer)

The polyamide elastomer layer contains a polyamide elastomer and, if desired, known additives and radio-opaque materials may also be contained, or the layer may be formed of at least one polyamide elastomer alone. The polyamide elastomers may be used singly or in combination of two or more. When the polyamide elastomer layer contains 50 to 100 wt % of a polyamide elastomer, there can be secured trackability and passage performance through a stenosed lesion area such as of a blood vessel, both desirable for the balloon, and flexibility desired for the dilation of a calcified lesion.

The average thickness of the polyamide elastomer layer can be 0.5 to 10 µm, for example, 1 to 5 µm. For example, when the average thickness is within a range of 0.5 to 10 µm, flexibility, passage performance and pressure resistance performance for use as a balloon can be well balanced.

The polyamide elastomer used as the polyamide elastomer layer can be made of a polyamide block copolymer, for example, a binary block copolymer having a hard segment and soft segment. As a binary block copolymer, mention can be made, for example, of a block copolymer of a polyamide (hard segment) and a polyether (soft segment). The binary block copolymer can include a block copolymer of nylon 11 and polytetramethylene glycol or a block copolymer of nylon 12 and polytetramethylene glycol.

The content of the soft segment in the polyamide elastomer can be 1 to 50 wt %, for example, 10 to 30 wt %.

The Shore D hardness of the polyamide elastomer can be 50 to 80, for example, 55 to 63.

The tensile elasticity of the polyamide elastomer can be 200 to 600 MPa, for example, 230 to 500 MPa.

For example, the polyamide elastomer can have, as a polymer chain, a block copolymer of the following chemical formula (1) or (2):

wherein a, b, c, d, p and q are independent from one another and a is an integer of 4 to 12, b is an integer of 4 to 10, c is an integer of 0 to 100, d is an integer of 0 to 100, p is an integer of 2 to 4, and q is an integer of 1 to 100, and Ln is a linker region and represents —C(O)—R—O—C(O)— wherein R is an alkylene group made of 2 to 12 methylene units, or wherein n, m, l, p and q are independent from one another and n is an integer of 5 to 11, l is an integer of 0 to 100, m is an integer of 0 to 100, p is an integer of 2 to 4, and q is an integer of 1 to 100, and Ln is a linker region and represents —C(O)—R—O—C(O)— wherein R is an alkylene group made of 2 to 12 methylene units.

The polyamide elastomer can be either a polyamide elastomer block copolymer per se of the above chemical formula (1) or (2), or a further polymerized one of the polyamide elastomer block copolymer of the chemical formula (1) or (2) by melt polymerization, of which the further polymerized one of the polyamide elastomer block copolymer of the chemical formula (1) or (2) by melt polymerization is exemplary. Accordingly, with the case of the polymer further polymerized by melt polymerization, the polyamide elastomer block copolymer of the chemical formula (1) or (2) can serve as a so-called "repeating unit."

R in the chemical formulas (1) and (2) is an alkylene group made of 2 to 12 methylene units, which may be linear, branched or cyclic and is thus not limited. Examples include a tetramethylene group, a 2-methylpropylene group, a 1,1-dimethylethylene group, an n-pentylene group, an n-hexylene group, an n-nonylene group, a 1-methyloctylene group, a 6-methyloctylene group, a 1-ethylheptylene group, a 1-(n-butyl)pentylene group, a 4-methyl-1-(n-propyl)pentylene group, a 1,5,5-trimethylhexylene group, a 1,1,5-trimethylhexylene group, an n-decylene group, a 1-methylnonylene group, a 1-ethyloctylene group, a 1-(n-butyl)hexylene group, a 1,1-dimethyloctylene group, a 3,7-dimethyloctylene group, an n-undecylene group, a 1-methyldecylene group and the like.

The further polymerized one can be obtained by melt polymerization of a polyamide elastomer whose terminal ends are not capped. The melt polymerization can be carried out by heating in a vacuum dryer having a cooling function (cooling machine: UT-4000L, made by Eyela Inc.) for a given time (5 to 80 hours) under a vacuum created by a vacuum pump (GCD136XN, made by Ulvac Inc.) at 200 to 280° C.

Where the polyamide elastomer block copolymer of the chemical formula (1) or (2) is used as the polyamide elastomer layer, the polyamide elastomer block copolymers of the chemical formula (1) or (2) may be used singly or in combination of two or more. In the case where the further polymerized polymer wherein the polyamide elastomer block copolymer of the chemical formula (1) or (2) serves as "repeating units" is used, the polyamide elastomer block copolymer of the chemical formula (1) or (2) may be mixed with the further polymerized polymer. Additionally, the repeating units of the chemical formulas (1) and (2) may be contained in the polymer chain of the further polymerized polymer.

The weight-average molecular weight of the polyamide elastomer can be 10,000 to 500,000, for example, 15,000 to 400,000, for example, 20,000 to 300,000. The molecular weight of the polyamide elastomer can be measured in the same manner as with the polyamide.

For example, when the weight-average molecular weight of polyamide elastomer is within a range of 10,000 to 500,000, the compliance characteristic can be improved because elongational viscosity is high and the elongation associated with pressurization is suppressed.

The polyamide elastomers may be synthesized, or commercial products may be employed including, for example, ELG5660 (commercial name: Grilflex, made by EMS Inc.), ELG6260 (commercial name: Grilflex, made by EMS Inc.), a high molecular weight product obtained by melt polymerization of the ELG5660 (melt viscosity: 1260 to 3489 Pa-second), a high molecular weight product obtained by melt polymerization of the ELG6260 (melt viscosity: 5282 to 7391 Pa-second) and the like.

The polyamide elastomer may be capped with a carboxyl group, an amino group or the like at terminal ends thereof.

In an exemplary embodiment, the melt viscosity of the polyamide elastomer is not less than 500 Pa-second, and can be, for example, 500 to 20,000 Pa-second. For example, the elongation associated with pressurization is more suppressed, thereby showing a better compliance characteristic as a whole of the balloon. It will be noted that the melt viscosity was measured by use of a flow tester (CFT-500D, made by Shimadzu Corporation).

The additives and radio-opaque materials, which may be contained in the polyamide elastomer layer, if desired, are the same as those used in the polyamide layer and are not repeated again.

In the section perpendicular to the axis of the balloon at an axial center thereof, a ratio of the sectional area of one polyamide elastomer layer to the whole sectional area of the balloon can be 5 to 25%, for example, 10 to 20%.

For example, in this range, the molecular weight distribution as a whole of the balloon can be set within a range of 3 to 10.

In an exemplary embodiment of the balloon materials, when the weight-average molecular weight of a polyamide ranges from 20,000 to 50,000, the weight-average molecular weight of a polyamide elastomer ranges from 20,000 to 500,000, nylon 12 is selected as the polyamide and a block copolymer of nylon 12 and polytetramethylene glycol are selected as the polyamide elastomer, the molecular weight distribution (Mw/Mn) can be readily set at from 3 to 10.

[Method for Making a Balloon]

An exemplary method for making a balloon according to an exemplary embodiment is now described. An exemplary method for making the balloon includes the steps of (1) forming a two-layered or three-layered polymer tube (parison) by co-extrusion of a polyamide layer and a polyamide elastomer layer, (2) axially stretching the parison at a temperature within a range of from a normal temperature (25° C.) to less than melting points of both polymers and biaxially stretching the stretched parison by radial inflation, and (3) cooling the inflated parison to a normal temperature to form a biaxially stretched balloon including a tubular film body whose inner diameter is substantially uniform, a tapered portion provided at opposite sides of the film body, respectively, and a connection portion provided at the respective tapered portions and connecting with a catheter.

For example, attention can be paid to the molecular weight distribution of the whole polymers forming the balloon film. When the balloon is made according to the biaxially stretching method, starting polymer materials may undergo decomposition by the influence of heat, so that the molecular weights and molecular weight distribution is lowered. For example, the molecular weight of the thus made balloon may lower by 20 to 40% relative to the molecular weight of the starting materials with the possibility that the molecular weight distribution becomes less than 3. Accordingly, while taking such possible effect of heat into account, it can be desirable to appropriately select a starting polyamide and polyamide elastomer.

The above exemplary steps (1) to (3) are described in detail.

Step (1)

The step 1 of forming a tubular parison from stretchable polymers can be performed by means of a general-purpose extruder molding machine equipped with a die. A polyamide elastomer, which has been further polymerized or not polymerized by melt polymerization according to such a method as stated above, and a polyamide are, respectively, provided for starting polymer material, and the starting polymer materials are thermally melted in the extruder at 180 to 300° C., respectively, in such a way that 1 to 30 parts by weight of the polyamide elastomer is used per 100 parts by weight of the polyamide, followed by co-extrusion of the polymer melts from the die thereby forming a tubular parison 27. The extrusion temperature is a temperature at which the polymers can be melted, and can be 180 to 300° C., for example, 200 to 280° C.

Step (2)

Figure 2:
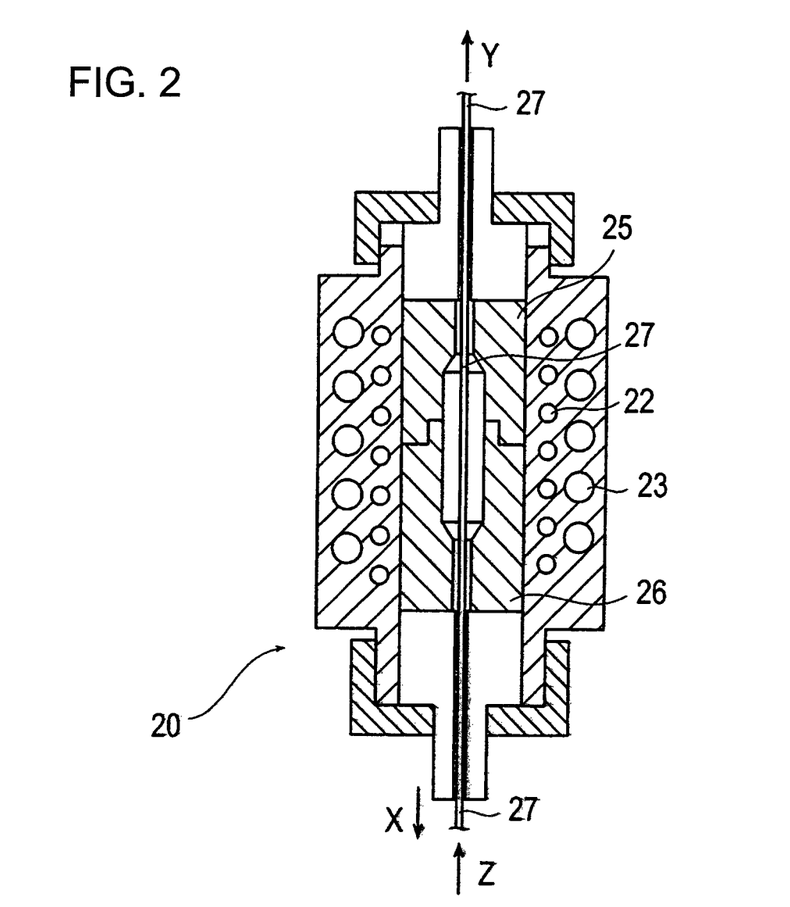
FIG. 2 is a schematic view illustrating a mold for a balloon, according to an exemplary embodiment.

This parison 27 is inserted into a mold 20 shown in FIG. 2 and is closed at one end of the parison 27. The closing is performed by thermal melting, high-frequency sealing, a clamp or the like. FIG. 2 is a sectional view of a balloon mold 20. This mold 20 has a heater 22 serving as a heating means, and a cooling pipe 23 serving as a cooling means. The mold 20 includes separable molds 25, 26 and the inner profile formed when these parts are combined together becomes a fundamental outer profile of a balloon to be formed.

As shown in FIG. 2, the heater 22 is switched on to heat the parison 27 at a portion where a balloon 11 is to be formed, to a temperature within a range of from a normal temperature to less than the melting points of the polymers (i.e., the polyamide and polyamide elastomer forming the parison 27), for example, within a range of from 70 to 140° C., for example, from 80 to 130° C. While keeping the parison 27 in the heated state, the parison 27 is stretched in directions of arrows X and Y, followed by feeding a gas under pressure into the parison 27 from the direction of arrow Z, under which the parison 27 at a portion heated in the mold 20 is brought into intimate contact with the inner wall surfaces of the separable molds 25, 26.

The pressure of the gas being fed into the parison 27 can be 2.0 to 6.0 MPa, for example, 2.5 to 5.0 MPa, for example, 3.0 to 4.5 MPa.

The stretching distances along the directions of arrows X, Y of the parison 27 can be 1 to 100 mm, for example, 2 to 80 mm, for example, 3 to 50 mm, respectively.

For example, in the case where the parison 27 is brought into intimate contact with the inner wall surfaces of the separable molds 25, 26, the inflation ratio is at 7 to 9 times for inner diameter and at 2 to 5 times for outer diameter as great as the diameter of the parison 27 prior to its insertion into the mold 20.

Step (3)

A liquid coolant is circulated through the cooling pipe 23 so that the parison 27 is cooled down to a normal temperature. The cooling may be natural cooling by mere standing without circulating a liquid coolant. Subsequently, the parison 27 is returned to a normal pressure therein and the parison 27 is removed from the mold 20. The parison 27 is cut off at the distal end portion and proximal end portion to form a fundamental shape of balloon as is shown in FIGS. 1A and 1B. If the above stretching operations are repeated twice or more, a balloon having an intended thickness may be formed.

[Balloon Catheter]

An exemplary, non-limiting embodiment relating to a balloon catheter is now described. In the drawings, like elements or members are indicated by like reference numerals and are not repeatedly illustrated. The dimensional ratios in the drawings are not necessarily to scale and are for convenience of illustration and may thus differ from actual ratios.

Figure 3:
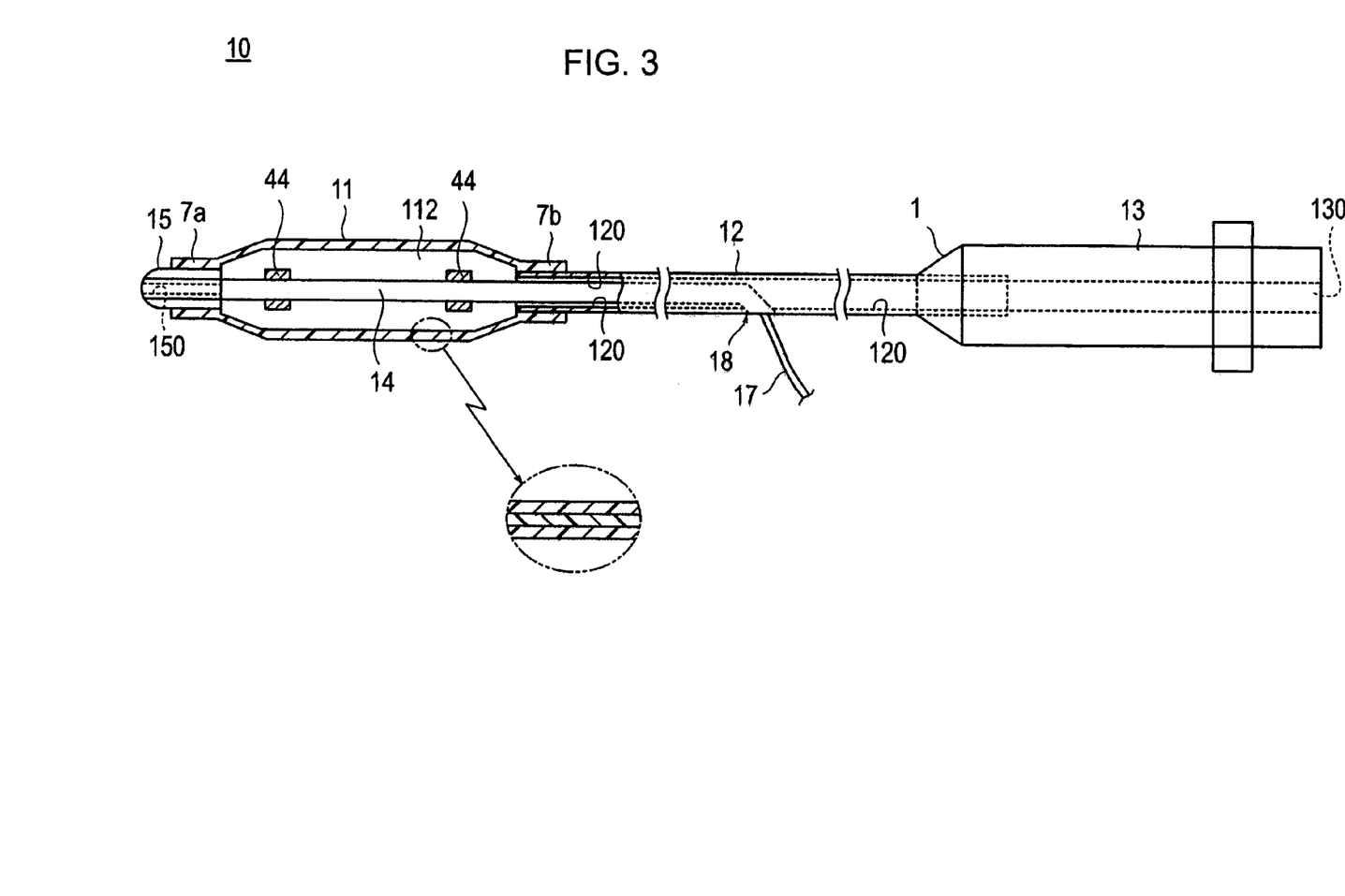
FIG. 3 is a schematic view showing a balloon catheter, according to an exemplary embodiment.

The balloon catheter is illustrated with reference to the accompanying drawing. FIG. 3 is a schematic view showing an example of a balloon catheter.

As shown in FIG. 3, a balloon catheter 10 has a catheter body 1 provided with an elongated outer tube 12 capable of transferring a fluid, a balloon 11 connected to a distal end of the catheter body 1, and a hub 13 attached to a proximal end of the catheter body 1. The balloon catheter 10 further includes an inner tube 14 passing through a lumen 120 formed in the outer tube 12, and a tip member 15 provided at a distal end of the inner tube 14. The term "distal end" means an end portion located at a side of being inserted into blood vessel when in use and the proximal end means an end portion located at a side of an operator operating the balloon catheter 10 when in use.

In FIG. 3, there is shown a catheter of a rapid exchange type in which a single lumen is formed at the proximal end portion side of the catheter and which is provided with a wire port permitting a guide wire to be inserted between the distal end and the proximal end. Alternatively, there may be used an over-the-wire catheter in which a coaxial double lumen is formed at the proximal end portion side and an inner tube thereof extends to a hub.

This balloon catheter 10 is an example applied as a vasodilation catheter. The balloon and balloon catheter can also be applied as other types of catheters including a urethral catheter.

The fluids to be fed from the catheter to the balloon include those known in the art such as a contrast agent, a helium gas, a physiological saline solution, a $CO_2$ gas, an $O_2$ gas, a $N_2$ gas, air and the like.

The structure of the balloon catheter 10 is described in more detail. As shown in FIG. 3, the balloon catheter 10 includes an inner tube 14 having a first lumen 150 whose distal end is open, an outer tube 12 coaxially provided with the inner tube 14 at a position located backwardly from a distal end of the inner tube 14 to a proximal end side by a given length and forming a second lumen 120 along with the outer surface of the inner tube 12, a foldable balloon 1, which has a connection portion (a distal end side of the balloon) 7a with the catheter and a connection portion (a proximal end portion side) 7b with the catheter wherein the connection portion 7b is attached to the outer tube 12 and the connection portion 7a is attached to the inner tube 14, and which is communicated with the second lumen 120 in the vicinity of the proximal end portion, and a hub having an opening communicated with the second lumen.

The balloon catheter 10 is composed of the catheter body 1 provided with the inner tube 14 and the outer tube 12, the hub 13 and the balloon 11. The inner tube 14 has the first lumen 150 (the outer lumen at the inner side) having an opening at the distal end thereof. The first lumen 150 is a lumen through which a guide wire is passed and is communicated with the wire port 18 that is an opening forming a guide wire port. The guide wire 17 can be passed through from the wire port 18.

As to the inner tube 14, the outer diameter can be 0.30 to 2.50 mm, for example, 0.40 to 2.00 mm, and the inner diameter can be 0.20 to 2.35 mm, for example, 0.25 to 1.70 mm. The materials for forming the inner tube 24 can be those having a degree of flexibility and can include, for example, thermoplastic resins such as polyolefin (e.g., polyethylene, polypropylene, ethylene-propylene copolymer, ethylene-vinyl acetate copolymer), polyvinyl chloride, polyurethane, polyamide, polyamide elastomer, polyester elastomer and the like.

The outer tube 12 allows the inner tube 14 to be passed therethrough and its distal end is provided at a position located slightly backwardly from the distal end of the inner tube, and the second lumen 120 is formed from the inner surface of the outer tube 12 and also from the outer surface of the inner tube 14. Accordingly, the second lumen 120 can be one having an adequate capacity. The second lumen 120 is communicated at the distal end thereof with the above-stated balloon 11 at the proximal end portion thereof. The proximal end of the second lumen 120 is communicated with the opening 130 of the hub 13, which forms an injection port for injecting a fluid capable of inflating the balloon (e.g., a contrast agent, a helium gas, a physiological saline solution, a $CO_2$ gas, an $O_2$ gas or the like). The outer tube 12 has an outer diameter in the range of 0.50 to 4.30 mm, for example, 0.60 to 4.00 mm and an inner diameter of 0.40 to 3.80 mm, for example, 0.50 to 3.00 mm.

If desired, such a radio-opaque material as mentioned before may be injected into the balloon at the time the balloon is inflated.

The materials for forming the outer tube 12 can be those having a degree of flexibility and include, for example, thermoplastic resins such as polyolefin (e.g., polyethylene, polypropylene, ethylene-propylene copolymer, ethylene-vinyl acetate copolymer), polyvinyl chloride, polyurethane, polyamide, polyamide elastomer, polyester elastomer and the like.

In FIG. 3, the balloon catheter 10 can have at its distal end a spherical tip member 15 that plays a role of assisting the catheter to follow a blood vessel and serves to prevent blood vessel walls from damaging.

The balloon 11 is foldable and can be folded around the outer periphery of the inner tube 14 in a non-inflated condition. The balloon 11 is one that is foldable as having a tubular body at least a part of which is in a cylindrical form having substantially a uniform diameter so as to allow a stenosed lesion of blood vessel to be readily dilated. The connection portion 7b of the balloon 11 is liquid-tightly fixed to the distal end portion of the outer tube 12 by means of an adhesive or by thermal fusion bonding. The connection portion 7a is also liquid-tightly fixed to the distal end portion of the inner tube 14.

As shown in FIG. 3, when inflated, the balloon 11 forms a space 112 between the inner surface of the balloon 11 and the outer surface of the inner tube 14. The space 112 communicates at a proximal end side thereof with the second lumen 120 throughout the whole circumference. In this way, since the second lumen having a relatively great capacity is communicated at the proximal end side of the balloon 11, it becomes easy to inject a fluid from the second lumen into the balloon 11. The balloon 11 used may be one mentioned above. Although the balloon 11 is formed of a three-layered film in FIG. 3, no limitation is placed thereon so far as the balloon is constituted of a film of two or more layers made of a polyamide layer or layers and a polyamide elastomer layer or layers.

In order to permit the position of the tubular film body of the balloon 11 to be confirmed under radiography, one or more X-ray markers 44 can be provided on the outer surface of the inner tube 14. As shown in FIG. 3, the X-ray marker 44 can be provided at the slightly proximal side relative to the fixed portion between the inner tube 14 and the balloon 11 and also at the slightly distal side relative to the fixed portion between the balloon 11 and the outer tube 12. In other words, the X-ray marker can be provided at opposite end portions of the tubular film body 2 of the balloon 1.

The X-ray marker 44 can be formed of a radio-opaque material such as, for example, gold, platinum, iridium, tungsten or an alloy thereof.

The hub 13 communicates with the second lumen 120 and has the opening 130 forming an injection port that is an inlet of a path through which a fluid is charged (supplied) or discharged. Thus, the opening 130 also serves as a flow passage and communicates, for example, to a fluid supply and discharge unit (not shown) such as an indeflator, a syringe, a pump or the like. Hence, a fluid is supplied to the balloon 11 via the opening 130 and the second lumen 120 or discharged from the balloon 11. For example, the opening 130 and the lumen 120 function as a supply and discharge path of a drive fluid inflating and deflating the balloon 11.

As a hub-forming material, there can be used thermoplastic resins such as polycarbonate, polyamide, polysulfone, polyallylate, methacrylate-butylene-styrene copolymer and the like.

EXAMPLES

In the examples, the measurement of molecular weight was made under the following conditions in all cases.
Mobile phase: hexafluoroisopropanol (+5 mmols/l $CF_3COONa$)
Reference material: standard polymethyl methacrylate (PMMA), dimethyl terephthalate
Injection amount: 100 μl
Flow rate: 1.0 ml/minute
Column temperature (measuring temperature): 40° C.
Concentration: 0.1 w/v %
Pretreatment: filtered through a 0.2 μm membrane filter
Apparatus used: pump Shodex DS-4 (made by Showa Denko K.K.)

Separation column : Shodex GPC HFIP-806M-+HFIP-803 (made by Showa Denko K.K.)
Detector Shodex RI-71 (made by Showa Denko K.K.)
In the examples, Mn means number-average molecular weight, Mw means weight-average molecular weight, and Mw/Mn means molecular weight distribution.

Example 1

A polyamide elastomer (PAE1, Mn=19,200, Mw=86,500 and Mw/Mn=4.51) obtained by melt polymerization of a polyamide elastomer (Glylamide ELG5660 made by EMS Corporation, Mn=10,300, Mw=27,200 and Mw/Mn=2.64) was prepared, followed by manufacturing at 250° C. a three-layered tube (inflation rate of inside diameter: 8.2 times, ϕ0.37×0.47×0.82×0.88 mm) including inner and outer layers, each made of PAE1 and an intermediate layer made of a polyamide (Glylamide L25 made by EMS corporation, Mn=19,100, Mw=42,700, Mw/Mn=2.24). Thereafter, blow molding was carried out by blowing dry nitrogen into the resulting tube (parison) at 110° C. at a pressure of 3.9 MPa for 30 seconds to obtain a balloon having an outer diameter of 3.00 mm, a thickness of 22.4 µm and a length of 15 mm. Subsequently, the balloon was dissolved in hexafluoropropanol (HFIP) as it is and subjected to measurement of molecular weight by the GPC method, revealing that Mn was 12,800, Mw was 41,000 and Mw/Mn was 3.20. The pressure resistance (burst pressure) of the balloon was 35.9 atm, and the compliance was 0.010 mm/atm.

Example 2

A polyamide elastomer (PAE1, Mn=19,200, Mw=86,500 and Mw/Mn=4.51) obtained by melt polymerization of a polyamide elastomer (Glylamide ELG5660 made by EMS Corporation, Mn=10,300, Mw=27,200 and Mw/Mn=2.64) was prepared, followed by manufacturing at 250° C. a three-layered tube (inflation rate of inside diameter: 8.6 times, ϕ0.35×0.46×0.77×0.83 mm) including inner and outer layers, each made of PAE1 and an intermediate layer made of a polyamide (Glylamide L25 made by EMS corporation, Mn=19,100, Mw=42,700, Mw/Mn=2.24). Thereafter, blow molding was carried out by blowing dry nitrogen into the resulting tube (parison) at 110° C. at a pressure of 3.9 MPa for 120 seconds to obtain a balloon having an outer diameter of 3.00 mm, a thickness of 22.1 µm and a length of 15 mm. Subsequently, the molecular weight was measured in the same manner as set out above, revealing that Mn was 12,800, Mw was 42,100 and Mw/Mn was 3.29. The pressure resistance (burst pressure) of the balloon was 36.9 atm, and the compliance was 0.010 mm/atm.

Example 3

A polyamide elastomer (PAE2, Mn=18,600, Mw=120,600 and Mw/Mn=6.48) obtained by melt polymerization of a polyamide elastomer (Glylamide ELG6260 made by EMS Corporation, Mn=10,600, Mw=24,700 and Mw/Mn=2.33) was prepared, followed by manufacturing at 250° C. a three-layered tube (inflation rate of inside diameter: 8.6 times, ϕ0.35×0.47×0.82×0.88 mm) including inner and outer layers, each made of PAE2 and an intermediate layer made of a polyamide (Glylamide L25 made by EMS corporation, Mn=19,100, Mw=42,700, Mw/Mn=2.24). Thereafter, blow molding was carried out by blowing dry nitrogen into the resulting tube (parison) at 110° C. at a pressure of 3.7 MPa for 30 seconds to obtain a balloon having an outer diameter of 3.00 mm, a thickness of 23.0 µm and a length of 15 mm. Subsequently, the molecular weight was measured in the same manner as set out above, revealing that Mn was 12,700, Mw was 49,300 and Mw/Mn was 3.88. The pressure resistance (burst pressure) of the balloon was 34.1 atm, and the compliance was 0.011 mm/atm.

Example 4

A polyamide elastomer (PAE2, Mn=18,600, Mw=120,600 and Mw/Mn=6.48) obtained by melt polymerization of a polyamide elastomer (Glylamide ELG6260 made by EMS Corporation, Mn=10,600, Mw=24,700 and Mw/Mn=2.33) was prepared, followed by manufacturing at 250° C. a three-layered tube (inflation rate of inside diameter: 8.6 times, ϕ0.35×0.47×0.82×0.88 mm) including inner and outer layers, each made of PAE2 and an intermediate layer made of a polyamide (Glylamide L25 made by EMS corporation, Mn=19,100, Mw=42,700, Mw/Mn=2.24). Thereafter, blow molding was carried out by blowing dry nitrogen into the resulting tube (parison) at 110° C. at a pressure of 3.7 MPa for 30 seconds to obtain a balloon having an outer diameter of 3.00 mm, a thickness of 23.0 µm and a length of 15 mm. Subsequently, the molecular weight was measured in the same manner as set out above, revealing that Mn was 12,700, Mw was 49,300 and Mw/Mn was 3.88. The pressure resistance (burst pressure) of the balloon was 33.3 atm, and the compliance was 0.012 mm/atm.

Example 5

A three-layered tube (inflation rate of inside diameter: 8.2 times, ϕ0.37×0.47×0.82×0.88 mm) was manufactured at 250° C. by using the same composition as in Example 1 except that there was used a polyamide (PA1, Mn=23,000, Mw=142,200 and Mw/Mn=6.18) obtained by melt polymerization of the polyamide (Glylamide L25 made by EMS corporation, Mn=19,100, Mw=42,700 and Mw/Mn=2.24) used as the intermediate layer of Example 1. Thereafter, blow molding was carried out by blowing dry nitrogen into the resulting tube (parison) at 110° C. at a pressure of 3.7 MPa for 30 seconds to obtain a balloon having an outer diameter of 3.00 mm, a thickness of 21.9 µm and a length of 15 mm. Subsequently, the molecular weight was measured in the same manner as set out above, revealing that Mn was 14,700, Mw was 93,100 and Mw/Mn was 6.33. The pressure resistance (burst pressure) of the balloon was 39.1 atm, and the compliance was 0.009 mm/atm.

Example 6

A three-layered tube (inflation rate of inside diameter: 8.6 times, ϕ0.35×0.46×0.77×0.83 mm) was manufactured at 250° C. by using the same composition as in Example 1 except that there was used a polyamide (PA1, Mn=23,000, Mw=142,200 and Mw/Mn=6.18) obtained by melt polymerization of the polyamide (Glylamide L25 made by EMS corporation, Mn=19,100, Mw=42,700 and Mw/Mn=2.24) used as the intermediate layer of Example 1. Thereafter, blow molding was carried out by blowing dry nitrogen into the resulting tube (parison) at 110° C. at a pressure of 3.9 MPa for 30 seconds to obtain a balloon having an outer diameter of 3.00 mm, a thickness of 23.4 µm and a length of 15 mm. Subsequently, the molecular weight was measured in the same manner as set out above, revealing that Mn was 14,600, Mw was 91,700 and Mw/Mn was 6.28. The pressure resistance (burst pressure) of the balloon was 38.7 atm, and the compliance was 0.010 mm/atm.

Comparative Example 1

A three-layered tube (inflation rate of inside diameter: 8.6 times, φ0.35×0.47×0.82×0.88 mm) was manufactured at 250° C. by using a polyamide elastomer (Glylamide ELG5660 made by EMS corporation, Mn=10,300, Mw=27,200 and Mw/Mn=2.64) as inner and outer layers and a polyamide (Glylamide L25 made by EMS corporation, Mn=19,100, Mw=42,700 and Mw/Mn=2.24) as an intermediate layer. Thereafter, blow molding was carried out by blowing dry nitrogen into the resulting tube (parison) at 90° C. at a pressure of 4.2 MPa for 30 seconds to obtain a balloon having an outer diameter of 3.00 mm, a thickness of 22.4 μm and a length of 15 mm. Subsequently, the molecular weight was measured in the same manner as set out above, revealing that Mn was 11,000, Mw was 28,000 and Mw/Mn was 2.55. The pressure resistance (burst pressure) of the balloon was 30.9 atm, and the compliance was 0.016 mm/atm.

Comparative Example 2

A three-layered tube (inflation rate of inside diameter: 8.6 times, φ0.35×0.47×0.82×0.88 mm) was manufactured at 250° C. by using a polyamide elastomer (Glylamide ELG6260 made by EMS corporation, Mn=10,600, Mw=24,700 and Mw/Mn=2.33) as inner and outer layers and a polyamide (Glylamide L25 made by EMS corporation, Mn=19,100, Mw=42,700 and Mw/Mn=2.24) as an intermediate layer. Thereafter, blow molding was carried out by blowing dry nitrogen into the resulting tube (parison) at 90° C. at a pressure of 4.2 MPa for 30 seconds to obtain a balloon having an outer diameter of 3.00 mm, a thickness of 21.7 μm and a length of 15 mm. Subsequently, the molecular weight was measured in the same manner as set out above, revealing that Mn was 11,000, Mw was 27,500 and Mw/Mn was 2.50. The pressure resistance (burst pressure) of the balloon was 23.1 atm, and the compliance was 0.019 mm/atm.

It should be understood by those skilled in the art that various modifications, combinations, sub-combinations and alterations may occur depending on design requirements and other factors. That is, the detailed description above describes features and aspects of embodiments of a balloon and a balloon catheter. The invention is not limited, however, to the precise embodiments and variations described. Various changes, modifications and equivalents may be implemented by one skilled in the art without departing from the spirit and scope of the invention as defined in the claims. It is expressly intended that all such changes, modifications and equivalents which fall within the scope of the claims are embraced by the claims.

What is claimed is:

1. A balloon, comprising a laminated film of at least two layers including a polyamide elastomer layer and a polyamide layer,
   wherein said polyamide elastomer layer is formed at an inner side of said polyamide layer,
   wherein a molecular weight distribution as a whole of said balloon, calculated by weight-average molecular weight Mw/number-average molecular weight Mn, is in a range of 3 to 10.

2. The balloon according to claim 1, wherein the molecular weight distribution as a whole of the balloon is in a range of 3 to 8.

3. The balloon according to claim 1, wherein each of the weight-average molecular weight of the polyamide of the polyamide layer and the weight-average molecular weight of the polyamide elastomer of the polyamide elastomer layer is not less than 40,000.

4. The balloon according to claim 1, further comprising a second polyamide elastomer layer formed at an outer side of said polyamide layer.

5. The balloon according to claim 1, wherein the polyamide layer includes nylon 11, nylon 12 or a combination thereof.

6. The balloon according to claim 1, wherein a weight-average molecular weight of the polyamide of the polyamide layer is in a range of 10,000 to 500,000.

7. The balloon according to claim 1, wherein an average thickness of the polyamide layer is in a range of 0.5 to 49.5 pm.

8. The balloon according to claim 1, wherein the polyamide elastomer layer contains a binary block copolymer, wherein the binary block copolymer is a block copolymer of nylon 11 and polytetramethylene glycol or a block copolymer of nylon 12 and polytetramethylene glycol.

9. The balloon according to claim 1, wherein a weight-average molecular weight of the polyamide elastomer of the polyamide elastomer layer is in a range of 10,000 to 500,000.

10. The balloon according to claim 1, wherein an average thickness of the polyamide elastomer layer is 0.5 to 10 μm.

11. The balloon according to claim 1, wherein the polyamide layer contains a radio-opaque material, or the polyamide elastomer layer contains a radio-opaque material, or each of the polyamide layer and the polyamide elastomer layer contains a radio-opaque material.

12. The balloon according to claim 1, wherein a ratio of a sectional area of the polyamide layer to a total sectional area of the balloon measured at a section perpendicular to the axis of the balloon, is in a range of 40 to 90%.

13. The balloon according to claim 1, wherein an average thickness of the balloon under deflated conditions is in a range of 5 to 50 μm.

14. The balloon according to claim 1, wherein a compliance of the balloon is not larger than 0.013 mm/atm.

15. The balloon according to claim 1, wherein a hydrophilic resin is coated or fixed to an outer surface of the balloon.

16. The balloon according to claim 1, wherein the balloon is covered on an outer surface thereof with a biocompatible material or an antithrombotic material.

17. A balloon catheter comprising the balloon according to claim 1.

18. A method of making the balloon according to claim 1, the method comprising:
   forming a multi-layered polymer tube by co-extrusion of a polyamide layer and a polyamide elastomer layer,
   axially stretching the tube at a temperature, wherein the temperature is in a range of from 25° C. to less than a melting point of the polyamide of the polyamide layer, and wherein the temperature is in a range of from 25° C. to less than a melting point of the polyamide elastomer of the polyamide elastomer layer,
   biaxially stretching the stretched tube by radial inflation, and
   cooling the tube.

* * * * *